United States Patent
Shepherd et al.

(10) Patent No.: US 6,274,100 B1
(45) Date of Patent: Aug. 14, 2001

(54) PROCESS IRRADIATOR

(75) Inventors: Joseph L. Shepherd; Thomas J. Shepherd, both of San Fernando, CA (US)

(73) Assignee: J.L. Shepherd & Associated, San Fernando, CA (US)

(*) Notice: Subject to any disclaimer, the term of this patent is extended or adjusted under 35 U.S.C. 154(b) by 0 days.

(21) Appl. No.: 09/434,215

(22) Filed: Nov. 4, 1999

Related U.S. Application Data

(60) Provisional application No. 60/107,260, filed on Nov. 5, 1998.

(51) Int. Cl.[7] .................................................. B01J 19/08
(52) U.S. Cl. .................. 422/186.3; 422/22; 250/492.1; 250/496.1; 250/455.11
(58) Field of Search ................. 422/186.3, 22; 250/492.1, 496.1, 455.11

(56) References Cited

U.S. PATENT DOCUMENTS 4,029,967 * 6/1977 Tetzlaff ................. 250/454
6,015,185 * 4/2000 Beers ..................... 422/22

* cited by examiner

Primary Examiner—Kishor Mayekar
(74) Attorney, Agent, or Firm—John E. Wagner; Robert C. Smith

(57) ABSTRACT

A process irradiator includes a heavily shielded, generally cylindrical, housing with a heavily shielded top. A radiation source includes source elements in several tubes extending from the top into a shielded storage cask below the center of the housing floor. A circular track concentrically positioned relative to the track guides a motor-driven carousel carrying a number of turntables which carry material to be irradiated, the turntables being rotatable on their axes. A heavy shielded door provides access to the turntables which are successively rotated on the carousel to a position adjacent the door opening. A lifting structure on the top includes two or more lifting devices which permit selective lifting of the source elements from the storage cask into the housing. Interlock controls prevent the door from opening and the carousel from rotating unless all source elements are stored in the storage cask.

20 Claims, 4 Drawing Sheets

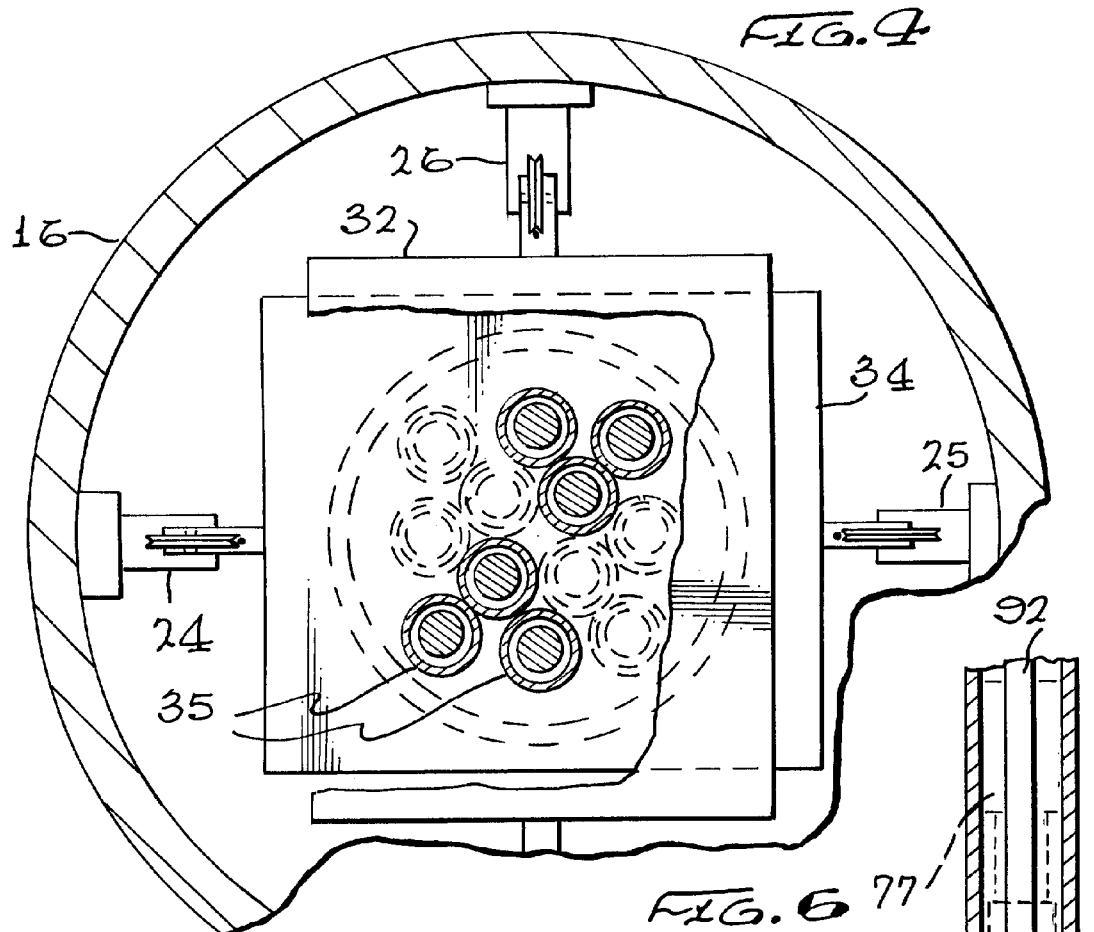
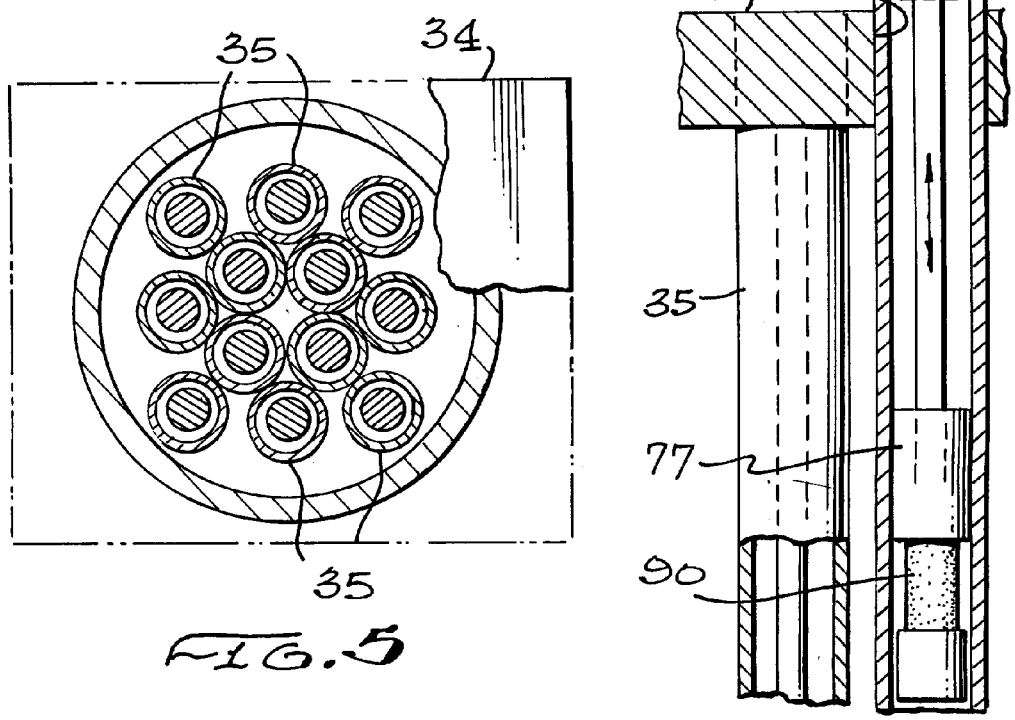

PROCESS IRRADIATOR

REFERENCE TO RELATED APPLICATION

This Non-provisional application claims benefit of U.S. Provisional Applications No. 60/107,260 filed Nov. 5, 1998.

BACKGROUND OF THE INVENTION

There is an established need for providing assurance of thorough and complete sterilization of medical equipment such as syringes, sutures, catheters, swabs, blood transfusion sets, petri dishes, scalpels and surgical gloves. These items have been routinely sterilized by cobalt 60 radiation. In addition it is useful to irradiate various food items with cobalt 60 radiation to retard spoilage and to assure that such products remain salable over a significant time period.

Because of danger of radiation damage to personnel, facilities for effecting the radiation have necessarily incorporated heavy shielded walls, floors and ceilings, which typically has required a separate building. To move the medical supplies or food items relative the radiation sources, expensive conveyor systems have been used. This combination of a separate building and an expensive conveyor system has resulted in a very costly installation. There is therefore a need for a simpler and less costly installation for providing process irradiation.

DESCRIPTION OF THE DRAWINGS

This invention may be clearly understood with the following detailed description and by reference to the drawings in which:

FIG. 4 is a sectional view taken along line 4—4 of FIG. 1;

FIG. 5 is a sectional view taken along line 5—5 of FIG. 1;

FIG. 6 is a fragmentary view, on an enlarged scale of two irradiation sources shown in FIG. 1.

SUMMARY OF THE INVENTION

Figure 1:
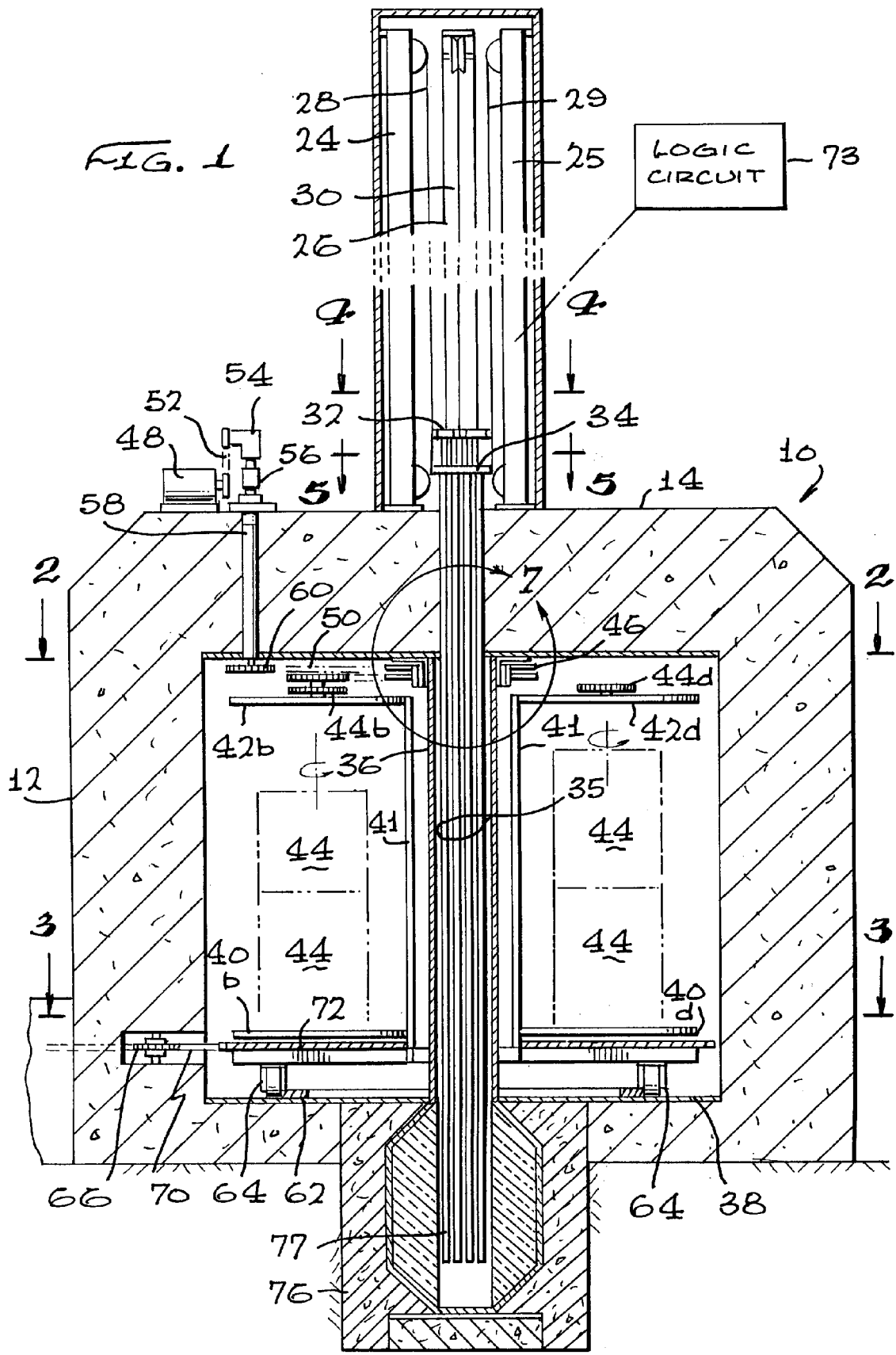
FIG. 1 is a vertical sectional view of our process irradiator.

Applicants have devised a process irradiator whose outside dimensions are only about the size of a medium sized room (15 ft.×20 ft.) and which can readily be installed in a dedicated area of an existing building. The irradiator is assembled from components, none of which weigh as much as 15000 pounds, which permits assembly using readily available industrial fork lift trucks.

In one embodiment the irradiation chamber consists of a housing consisting of a generally cylindrical concrete wall 72 inches thick and having an opening on one side with a heavy shielding door. The door is mounted on a track such that it can be moved laterally to open or close the opening. A roof which is also of concrete 72 inches thick is supported on the generally cylindrical wall and on the top of the door. Centered in the floor of the irradiation chamber is a cylindrical shielded storage cask which is set in the ground and which is approximately 30 inches in diameter and 30 inches deep. Shielding for the cask is void free lead contained in a welded steel enclosure. The radiation sources are stored in tubes which extend from within the storage cask to which they are bolted to the ceiling where they are attached to additional tube sections which extend through the roof section to the drive or lift system which drives the radiation sources up and down within the tubes. The source drive system is mounted on the rooftop and is an electro-pneumatic system utilizing cable cylinders operated by solenoid valves for precise positioning. There may be two or more sets of sources which are driven separately or in any desired combination.

Surrounding the source tube array and concentric to the array is a circular track or rail carrying a rotatable carousel to which are attached a plurality, typically four, of turntables. Each turntable is driven rotatably by means of rotatable drive system. A clutch locks the turntables in place for engagement with the drive system. When the clutch is disengaged, the turntables can be moved around the rail to a position adjacent to the opening so that containers carrying the material to be irradiated can be separately placed on, or removed from, the turntables. When the turntables are all loaded with containers, the clutch is engaged so that the turntables can be rotated and the contents of the containers irradiated from the sources. Thus there are four turntables, each substantially equidistant from the source tubes, carrying containers which are being uniformly irradiated on all sides.

Various controls are provided to, inter alia, control the height of the sources to vary radiation levels and to provide interlocks such that the sources cannot be lifted from the storage cask until the door is closed and locked and the door cannot be opened until the sources are all properly housed in the storage cask. The source rods may be grouped so that different levels of radiation may be selected. A second embodiment is similar to that described above except that the cylindrical wall, roof and door are made of steel plates 30 inches apart and with the space between the plates filled with steel material such as steel shot. A third embodiment is similar to that described above except that the inner cylindrical wall and roof are made of steel plate, and earthen shielding is used for the wall and roof. This embodiment also uses a thick steel door as described above.

DESCRIPTION OF THE PREFERRED EMBODIMENT

Referring now to FIG. 1, which is a vertical sectional view of the process irradiator of the invention, the processor includes a housing 10 which is of generally cylindrical conformation having a concrete sidewall 12 approximately 72 inches thick and a top 14, also of concrete approximately 72 inches thick. Carried on top 14 is a tower 16 which contains a lifting structure including cylinders 24, 25 and 26 connected through cables 28, 29 and 30 to a pair of lifting blocks 32 and 34. Another cylinder and cable are not visible in this view. Each of blocks 32 and 34 carry a plurality of cobalt 60 sources which are supported on cables movable within a plurality of stainless steel guide tubes 35. Tubes 35 are, in turn, located within and protected by a perforated cylindrical steel housing 36 which extends from top 14 through the floor 38 of the process irradiator 10. Also visible in this view are a plurality of turntables 40b and 40d. Turntables 40b and 40d are connected by means of a plurality of vertical supports 41 to circular drive members 42b and 42d located near the top of housing 10 which carry chain sprockets 44b and 44d, respectively. Only a single vertical support 41 is shown connected between turntables 40b and drive member 42b and between turntable 40d and drive member 42d to avoid confusing the drawing. The numbers and locations of such supports will be obvious to those skilled in the art, it only being necessary to allow clearance for loading the turntables. The chain sprockets are part of a chain drive system, discussed in detail below, which includes a double sprocket idler assembly 46. A motor 48 drives a chain 50 connected to assembly 46 through a belt or chain drive 52 to a right angle drive 54, a clutch 56 and a shaft 58 terminating in a sprocket 60.

On the floor 38 of housing 10 is a circular guide rail 62 which guides a plurality of rigid casters 64 around its periphery to assure that the turntables move around in the desired circle within housing 10. Connected to motor 48 or another suitable motor is a sprocket 66 which transmits power through a chain 70 which serves to drive a rotatable carousel 72 upon which all the turntables are supported and rotated.

Block 73 shown connected to tower 16 contains controls including a central data processor and input devices which provide such functions as raising and lowering the cobalt 60 sources only when door 18 is closed, opening door 18 only when the sources are safely stored in the storage cask 76 etc.

Figure 2:
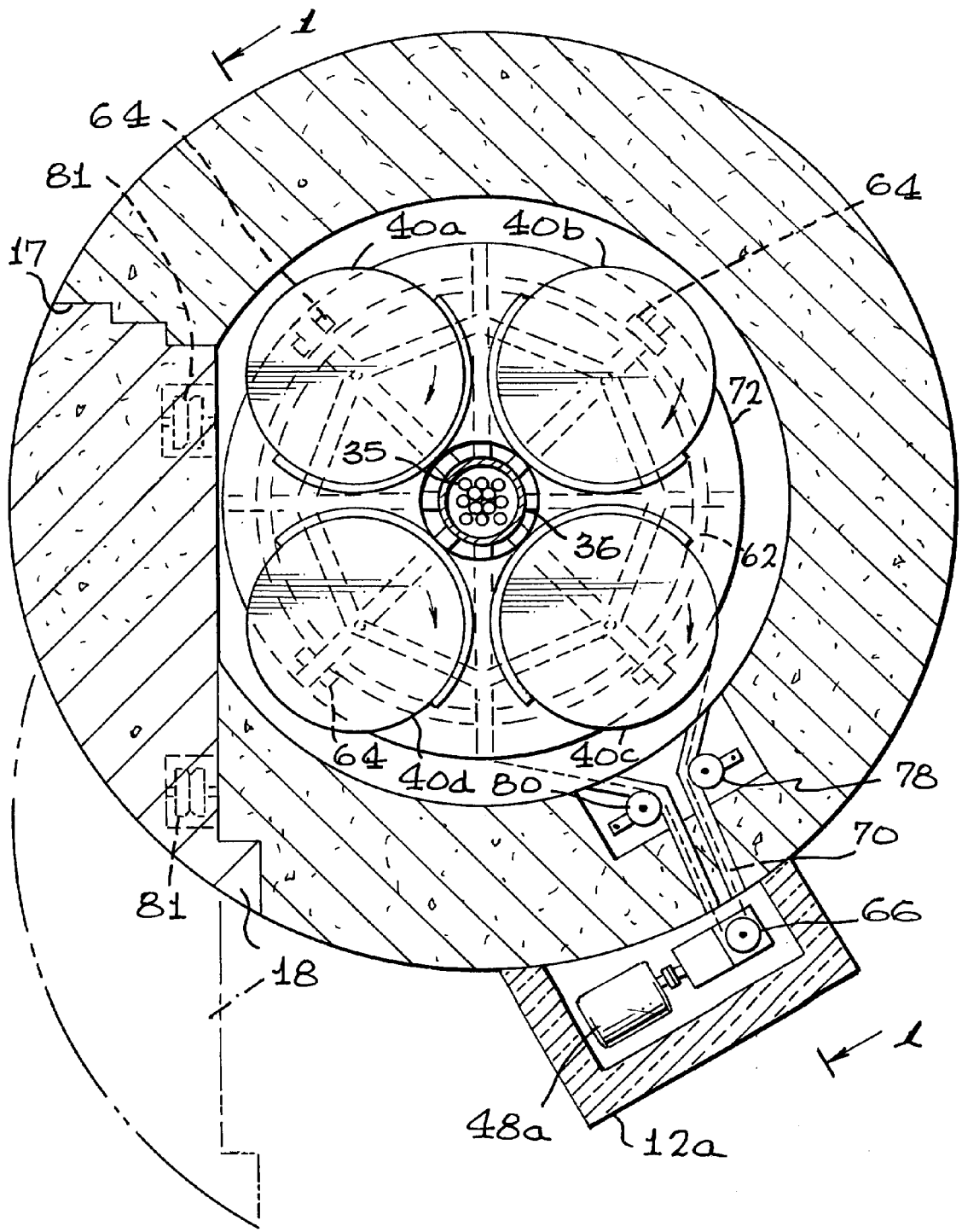
FIG. 2 is a sectional view taken along line 2—2 of FIG. 1.

The structure in housing 10 is more clearly shown in FIG. 2 which is a sectional view taken along line 2—2 of FIG. 1. Shown in this view is housing 10, turntables 40a, 40b, 40c and 40d, and the steel guard housing 36 shown enclosing a plurality of guide tubes 35.

Turntables 40a, 40b 40c and 40d are movable on carousel 72 around circular rail 62 to a position adjacent an opening 17 and door 18 for loading and unloading of containers 44 which contain the material to be irradiated. The containers are dimensioned to fit on the turntables without interference with either the interior surface of sidewall 12 or guard housing 36 and can be stacked two or three high on the turntables. To avoid interference with door 18 which is closed during irradiation, the carousel 72 is rotated 45 degrees from the loading/unloading position as shown. If the material to be irradiated is supplied with other packaging, such packaging must be placed within the containers. Preferably, the turntables and the bottoms and tops of the containers 44 have mating grooves or projections to assure that the containers are properly positioned on the turntables and on each other. Since containers 44 are generally loaded on to the turntables by means of a forklift truck such grooves or projections should preferably be positioned to accommodate the tines of the forklift.

The cobalt 60 sources are suspended on rigid members movable within the guide tubes 35. When the sources are not in use actively irradiating the contents of materials in the containers 44, they are stored in a storage cask 76 which is buried in and below the level of floor 38 and directly below tower 16. This storage cask is of void free lead lined with steel and is approximately 30 inches in diameter and 30 inches deep. Each of the sources includes a plug of tungsten shielding material 77 above the cobalt 60 material which effectively shields the inside of housing 10 from radiation from storage cask 46. This shielding is sufficient to keep radiation levels within housing 10 to less than 5 mRem/hr at 12 inches directly above the cask around the cask protective housing 36 when the sources are in stored position in cask 46.

The carousel 72 may be driven by means of motor 48 or another motor 48a shown secured in a shielded housing 12a to attached sidewall 12 and which drives a chain 70 which travels in tubes through sidewall 12. Chain 70 wraps around the carousel 72 causing the carousel 72 to rotate from one loading and unloading position to the next. Certain supports and braces are shown in dashed lines which are positioned under and tend to support the carousel 72. A pair of tensioners 78, 80 serve to keep chain 76 taut. This view also shows, in phantom, the circular rail 62 and a plurality of casters 64 which are positioned at intervals under each of the radial braces supporting carousel 72.

Door 18 is movable to open and close opening 17 for loading and unloading. Since door 17 it is extremely heavy it is driven by motor 48 or other motor means on rollers 81 along a track. When the door 18 is open the containers may be loaded/unloaded onto or from the turntables by means of a forklift truck. Once one turntable is loaded, for example, the carousel is rotated 90° to place the next turntable in position for loading, etc. When all turntables are loaded, door 17 is closed carousel 27 is rotated 45° to clear door 18 and irradiation may begin.

Figure 3:
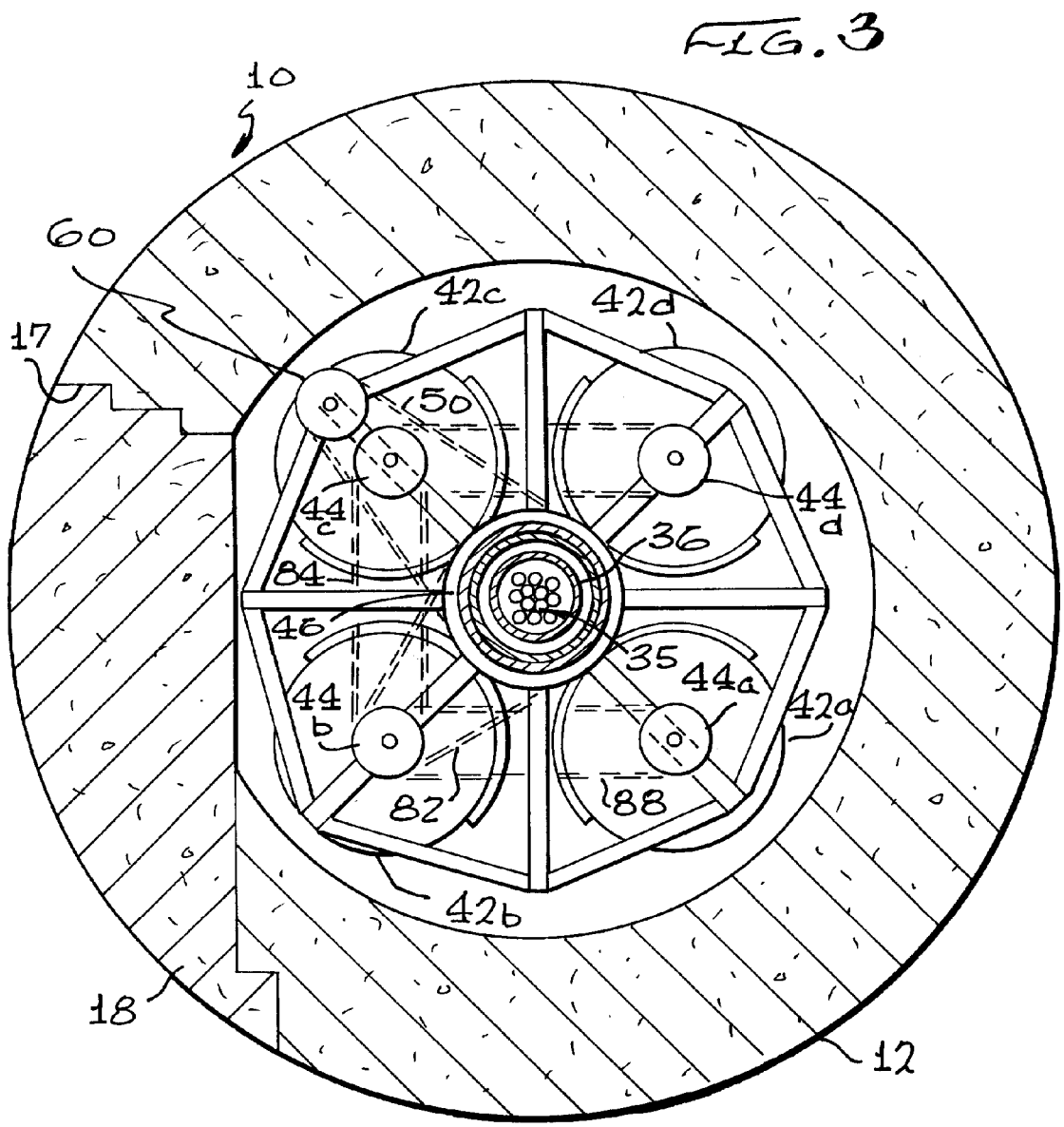
FIG. 3 is a sectional view taken along line 3—3 of FIG. 1.

FIG. 3 is a sectional view taken along line 3—3 of FIG. 1 and shows details of the drive structure for rotating drive wheels 42a 42b 42c and 42d which rotate turntables 40a, 40b, 40c and 40d. The main drive sprocket 60 drives chain 50 to rotate the double sprocket idler assembly 46. A sprocket coaxial with the driven sprocket of assembly 46 drives a chain 82 which, in turn, drives sprocket 44b which rotates member 42b and, hence, turntable 40b. Another sprocket coaxial with sprocket 44b drives a chain 84 to drive a sprocket 44c, which, in turn, drives a coaxial sprocket, driving a chain 86 to rotate sprocket 44d. A second sprocket coaxial with sprocket 44b drives a chain 88 to rotate a sprocket 44a. In this way sprockets 44b, 44c, 44d and 44a serve to rotate members 42b, 42c, 42d and 42a, respectively, thereby rotating turntables 40b, 40c, 40d and 40a respectively. When the irradiation is completed the cobalt 60 sources are lowered into the storage cask 76 and door 18 may be opened and the containers 44 removed from the turntables. If there are more containers having materials to be irradiated the containers can be removed and replaced while each turntable is in position adjacent opening 17.

FIG. 4 is a view, partly in section, taken along line 4—4 of FIG. 1. In this view one is looking down on lifting blocks 32 and 34 within the tower 16. A plurality of cobalt 60 sources are suspended from each of blocks 32 and 34 with one group (crosshatched) being suspended from block 32 and another group (in phantom) being suspended from block 34. Block 32 is physically positioned above block 34 and carries a group of stainless steel guide tubes 35 having rigid members or rods connected to cobalt 60 sources contained within them. If it is desired to expose one or more containers to only the sources connected to block 32, for example, block 32 is raised by means of actuator 25 and cable 30 and a corresponding actuator and rods not visible in FIG. 1. The guide tubes 35 connected to block 32 pass through ports in block 34 as shown in FIG. 6.

If a greater intensity of radiation is desired, both blocks 32 and 34 may be raised to lift all the sources out of storage cask 72.

FIG. 5 is a cross-sectional view taken along line 5—5 of FIG. 1. This view show both sets of source rods within their guide tubes 35 with rods from the groups cross-sectioned differently.

FIG. 6 is a fragmentary view on an enlarged scale of a pair of guide tubes 35 one connected to block 32 and the other connected to block 34 (not shown). A cobalt 60 source 98 is shown connected to a cable 92 which is connected to block 32. A second guide tube 35 is secured to block 34. This view shows that guide tubes 35 connected to block 32 are movable through ports 94 in block 34 to permit the sources connected to block 32 to be raised and lowered by moving through the ports 92 while leaving the guide tubes connected to block 34 stationary. This view also shows a tungsten shielding plug 77 in phantom in an alternate raised position.

Figure 7:
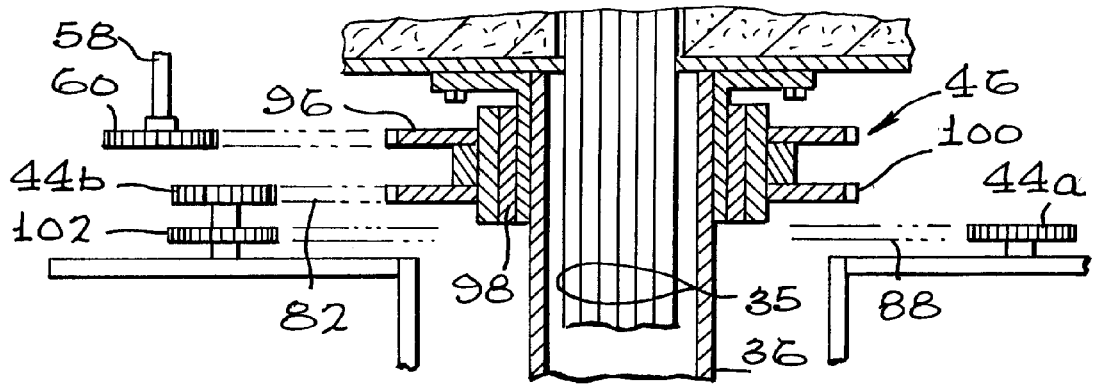
FIG. 7 is a fragmentary sectional view, on an enlarged scale, of the circled part of FIG. 1.

FIG. 7 is an enlarged fragmentary view partly in section of the circled portion of FIG. 1. The sprocket 60 drives a larger sprocket 96 which rotates around a bearing 28. A second large sprocket 100 is connected through chain 82 to drive sprocket 44b. Coaxial with sprocket 44b is another sprocket 102 which drives sprocket 44a through chain 88.

The above described embodiments of the present invention are merely descriptive of its principles and are not to be considered limiting. The scope of the present invention instead shall be determined from the scope of the following claims including their equivalents.

What is claimed is:

1. A process irradiator comprising a generally cylindrical shielded housing having a floor, a wall, a top, an opening in said wall and a door for closing said opening;
   a shielded storage cask;
   a radiation source in said housing movable between said storage cask and an irradiating position in said housing, said radiation source comprising a plurality of source elements and a plurality of tubes containing and guiding said source elements;
   a plurality of turntables and means for rotating said turntables substantially equidistant from said source; and
   means for successively moving said turntables to a position adjacent to said door.

2. A process irradiator as claimed in claim 1 wherein a perforated cylindrical member is positioned concentrically around said tubes.

3. A process irradiator as claimed in claim 1 further comprising shielding material in said tubes above said source elements such that when said sources are in said storage cask a minimum of radiation is present in said housing.

4. A process irradiator as claimed in claim 1 further comprising interlock controls such that said door cannot be opened unless said sources are in their fully shielded position and said sources cannot be moved to their unshielded position in said housing unless said door is closed and locked and which prevent said door from closing unless all said turntables are moved to positions away from said door.

5. A process irradiator as claimed in claim 1 wherein said means for successively moving said turntables comprises a track and rotatable concentrically around said radiation source on said track and said turntables are positioned on said carousel.

6. A process irradiator as claimed in claim 5 wherein said means for rotating said turntables comprises a motor positioned on said top.

7. A process irradiator as claimed in claim 6 further comprising a separate drive motor for driving said carousel.

8. A process irradiator as claimed in claim 1 wherein said wall and top are of steel plate and shielding for said wall and said top are of earth.

9. A process irradiator as claimed in claim 1 wherein said source elements and tubes are arranged in groups and a separate lifting fixture is attached to each group such that said groups of source elements and tubes may be selectively raised into said housing from said storage cask.

10. A process irradiator comprising a generally cylindrical shielded housing, an opening in said housing and a door movable to open and close said opening;
    a shielded storage cask;
    a source of radiation and a structure for moving said source between a shielded position in said storage cask and an irradiating position in the inside of said housing, said source of radiation being generally centered in said housing;
    a generally circular track positioned concentrically outwardly of said source;
    a carousel movable to a plurality of positions along said track around said source of radiation; and
    a plurality of turntables carried on said carousel and rotatable on their axes.

11. A process irradiator as claimed in claim 10 wherein said radiation source comprises a plurality of source elements and a plurality of tubes containing and guiding said source elements.

12. A process irradiator as claimed in claim 11 further comprising shielding material in said tubes above said source elements such that when said sources are in said storage cask a minimum of radiation is present in said housing.

13. A process irradiator comprising a shielded housing having a floor, a wall, a top and an opening;
    shielding material, a shielded storage cask below said housing and a radiation source in said housing movable between a shielded position in said storage cask and an unshielded position within said housing, said radiation source comprising a plurality of source elements and a plurality of tubes containing and guiding said source elements;
    a perforated cylindrical member positioned concentrically around said tubes;
    a lifting structure for raising said source elements from said storage cask to the interior of said housing and returning said source elements to said storage cask;
    a generally circular track in said housing positioned concentrically outwardly of said source;
    a plurality of turntables movable to a plurality of positions along said track, said turntables being rotatable in position;
    a shielded door closing said opening and providing access when open to one of said turntables when said turntable is moved to a position adjacent said door; and
    containers carried on said turntables for containing material to be irradiated.

14. A process irradiator as claimed in claim 13 wherein said lifting structure is positioned above said top and comprises electro-pneumatically-powered cable cylinders.

15. A process irradiator as claimed in claim 13 wherein said source elements and tubes are arranged in groups and a separate lifting fixture is attached to each group such that said groups of source elements and tubes may be selectively raised into said housing from said storage cask.

16. A process irradiator as claimed in claim 15 wherein each group of sources is connected to a block and one of said blocks includes ports permitting tubes of another of said groups to extend through said ports.

17. A process irradiator as claimed in claim 15 further comprising shielding material in said tubes above said source elements such that when said sources are in said storage cask a minimum of radiation is present in said housing.

18. A process irradiator as claimed in claim 13 further comprising interlock controls such that said door cannot be closed until said carousel is rotated to carry said turntables away from a door open position.

19. A process irradiator comprising a generally cylindrical shielded housing having an opening and a door for closing said opening;
   a shielded storage cask;
   a source of radiation generally centered in said housing and movable between said storage cask and an irradiating position in said housing;
   a circular track in said housing positioned concentrically outwardly of said source;
   a plurality of turntables and means for rotating said turntables on their axes;
   a carousel movable to a plurality of positions along said track carrying said turntables concentrically with respect to said irradiation source; and
   interlock controls which prevent said door from closing unless said carousel is rotated away from a door open position.

20. A process irradiator as claimed in claim 19 wherein said radiation source comprises a plurality of source elements and a plurality of tubes containing and guiding said source elements.

* * * * *

UNITED STATES PATENT AND TRADEMARK OFFICE
CERTIFICATE OF CORRECTION

PATENT NO. : 6,274,100 B1
DATED : August 14, 2001
INVENTOR(S) : Joseph L. Shepherd and Thomas J. Shepherd It is certified that error appears in the above-identified patent and that said Letters Patent is hereby corrected as shown below:

<u>Title page,</u>
Please correct Assignee, from "J.L. Shepherd & Associated" to -- J.L. Shepherd & Associates --

Signed and Sealed this

Thirtieth Day of April, 2002

*Attest:*

*Attesting Officer*

JAMES E. ROGAN
*Director of the United States Patent and Trademark Office*